(12) United States Patent
Brankov (10) Patent No.: US 7,412,870 B2
(45) Date of Patent: Aug. 19, 2008

(54) METHOD AND APPARATUS FOR DYNAMIC IMPACT TESTING

(75) Inventor: Anguel S. Brankov, San Jose, CA (US)

(73) Assignee: California Micro Devices, Milpitas, CA (US)

( * ) Notice: Subject to any disclaimer, the term of this patent is extended or adjusted under 35 U.S.C. 154(b) by 0 days.

(21) Appl. No.: 11/293,030

(22) Filed: Dec. 2, 2005

(65) Prior Publication Data

US 2007/0125152 A1 Jun. 7, 2007

(51) Int. Cl.
*G01N 3/48* (2006.01)
*G01N 3/32* (2006.01)
*G01N 3/42* (2006.01)

(52) U.S. Cl. .............................. 73/12.11; 73/81; 73/82
(58) Field of Classification Search .............. 73/12.01, 73/12.05, 12.06, 81, 12.09, 12.11, 12.13, 73/82, 83
See application file for complete search history.

(56) References Cited

U.S. PATENT DOCUMENTS

| 3,187,739 | A | * | 6/1965 | Du Fresne | 125/23.01 |
| 3,557,603 | A | * | 1/1971 | Carr | 73/12.04 |
| 3,879,982 | A | * | 4/1975 | Schmidt | 73/12.01 |
| 4,054,050 | A |  | 10/1977 | Reid |  |
| 4,313,337 | A | * | 2/1982 | Myint | 73/12.13 |
| 4,498,451 | A | * | 2/1985 | Beltz et al. | 125/23.01 |
| 4,930,355 | A | * | 6/1990 | Heck | 73/840 |
| 5,625,154 | A |  | 4/1997 | Matsuhiro et al. |  |
| 5,770,791 | A |  | 6/1998 | Manahan, Sr. |  |
| 5,824,880 | A | * | 10/1998 | Burwell et al. | 73/12.06 |
| 5,992,242 | A |  | 11/1999 | Murphy et al. |  |
| 6,389,876 | B1 |  | 5/2002 | Tanimura et al. |  |
| 6,523,391 | B1 | * | 2/2003 | Knox et al. | 73/12.06 |
| 2003/0140684 | A1 | * | 7/2003 | Broz et al. | 73/81 |
| 2004/0134263 | A1 | * | 7/2004 | Tsujii et al. | 73/81 |
| 2006/0138599 | A1 | * | 6/2006 | Thompson | 257/629 |

OTHER PUBLICATIONS

Alaca B E, Selby J C, Saif M T A, Sehitoglu H. 2002. Biaxial testing of nanoscale films on compliant substrates: Fatigue and fracture. Review of Scientific Instruments 73 pp. 2963-2965.*
Lawn, B R, Marshal D B, Chantikul P. 1981. Mechanics of strength—degrading contact flaws in silicon. Journal of Materials Science. 16 pp. 1769-1775.*

* cited by examiner

*Primary Examiner*—Edward Lefkowitz
*Assistant Examiner*—Punam Patel
(74) *Attorney, Agent, or Firm*—Pillsbury Winthrop Shaw Pittman LLP (57) ABSTRACT

A method and apparatus wherein a material or object to be tested is placed on a base support. A stopper assembly having a stopper tip on one end in contact with the test material or object, and a washer on the opposite end attached to a rod. A projectile is propelled with a selected level of force along the rod and impacts the washer, which transmits the force of impact through the stopper tip to the test material or object. The level of propelling force, the mass of the projectile, the construction of the stopper assembly and the location of impact on the test material or object may be precisely adjusted to simulate real-life impacts.

19 Claims, 7 Drawing Sheets

METHOD AND APPARATUS FOR DYNAMIC IMPACT TESTING

BACKGROUND OF THE INVENTION

1. Field of the Invention

The present invention relates generally to methods and apparatus for dynamic impact testing of materials or objects and more particularly to a method and apparatus for dynamic impact testing of materials or objects when force is applied to the materials or objects by impact with an accelerated projectile. The present invention has particular application in testing materials and objects related to integrated circuit (IC) production.

2. Description of the Prior Art

Dynamic impact testing is a load displacement test method in which a material or object is subjected to an impact force. The purpose of the dynamic impact test is to determine the resilience of a material or object under rough handling. Dynamic impact testing is often performed to ascertain the level of force required to cause the structure of a material or object to fail. Dynamic impact testing typically involves dropping a projectile from a height onto a test specimen and performing a subsequent inspection of the specimen.

Materials and objects used in the manufacture of semiconductor ICs are measured in inches or fractions of inches and dynamic impact testing of such materials and objects has, in the prior art, often been considered impractical because of the small size of the materials and objects.

SUMMARY

An embodiment of the present invention includes a method and apparatus for performing an impact test on a material or object wherein a projectile falls under the force of gravity until it strikes a stopper assembly that transmits the force of impact to the test materials or objects. The projectile can be axially mounted on a vertical or inclined rod to which the stopper assembly is attached at the lower end. The stopper assembly is typically formed by attaching a tip and a washer to the base of the rod so that the washer is located between the tip and the lower end of the rod. The stopper assembly tip may be positioned such that it contacts the surface of the test material or object. During impact testing, the projectile is typically propelled toward the stopper assembly and, upon striking the projectile, the energy of impact may be transmitted through the washer causing the stopper tip to impact the test material or test object.

Actual environmental conditions can be simulated through modification of the stopper assembly. The shape and mass of the projectile may be altered. The stopper assembly is typically configured to be easily attached or removed from the lower end of the rod thereby allowing the apparatus to be readily adapted for testing a wide variety of materials and objects, including: metals, ceramics, semiconductors, semiconductor wafers, insulators, ICs, IC dies and printed circuit boards. Further, the tip of the stopper assembly may be constructed in a variety of shapes, permitting the area of impact to be finely controlled. The tip of the stopper assembly can be manufactured from a variety of materials possessing different hardness, elasticity and other properties. The diameter and profile of the stopper assembly washer may be varied to ensure optimal transfer of energy to the selected stopper tip. In certain embodiments, the stopper tip contacts the test material or object prior to impact by the projectile thereby allowing the force of impact to be directed with precision to a selected point or area of impact on the test material or object.

Typically, the level of impact force imparted to the stopper assembly can be precisely controlled and measured. Thus, the apparatus is capable of accurately simulating actual environmental conditions observed in real-life impacts, including the impact experienced by falling materials or objects.

Various embodiments of the invention perform dynamic impact testing by propelling the projectile using a combination of forces including the forces derived from gravity, vacuum, electric magnetic, hydraulic, pneumatic, chemical reaction or other suitable source. The force of impact applied to the test material or object is selected by controlling the propulsion force applied to the projectile.

Embodiments of the invention direct a projectile towards the stopper assembly and test material or object using a variety of means, including but not limited to rods, tracks and rails. The means of directing the projectile may be oriented vertically, horizontally or at an incline.

In certain embodiments, a method for testing a material or object includes a sequence of impacts where the projectile is released from a selected height, vertically above the test material or object. In many embodiments, the projectile is initially released from a first height calculated to be less than the height required to generate sufficient energy to cause the structural failure of the test material or object. Subsequent impacts are caused where the projectile is released from incrementally greater heights until the test material or object suffers structural failure. The release height that caused structural failure is recorded and the associated energy imparted of impact is calculated using a formula such as $e=mgh$, where $e$ is the calculated energy, $m$ is the mass of the projectile and $h$ is the release height at which failure occurred. Thus, the force of impact is set by altering a combination of the release height and the mass of the projectile.

In certain embodiments, a test method includes a sequence of impacts comprising a fixed number of impacts to each of a group or batch of test materials or objects where an identical impact force is used for every impact.

In certain embodiments dynamic impact testing can be automated using return mechanisms and programmed sequences of impacts.

DETAILED DESCRIPTION OF PREFERRED EMBODIMENTS

Embodiments of the present invention will now be described in detail with reference to the drawings, which are provided as illustrative examples so as to enable those skilled in the art to practice the invention. Notably, the figures and examples below are not meant to limit the scope of the present invention. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. Further, the present invention encompasses present and future known equivalents to the components referred to herein by way of illustration.

Figure 1:
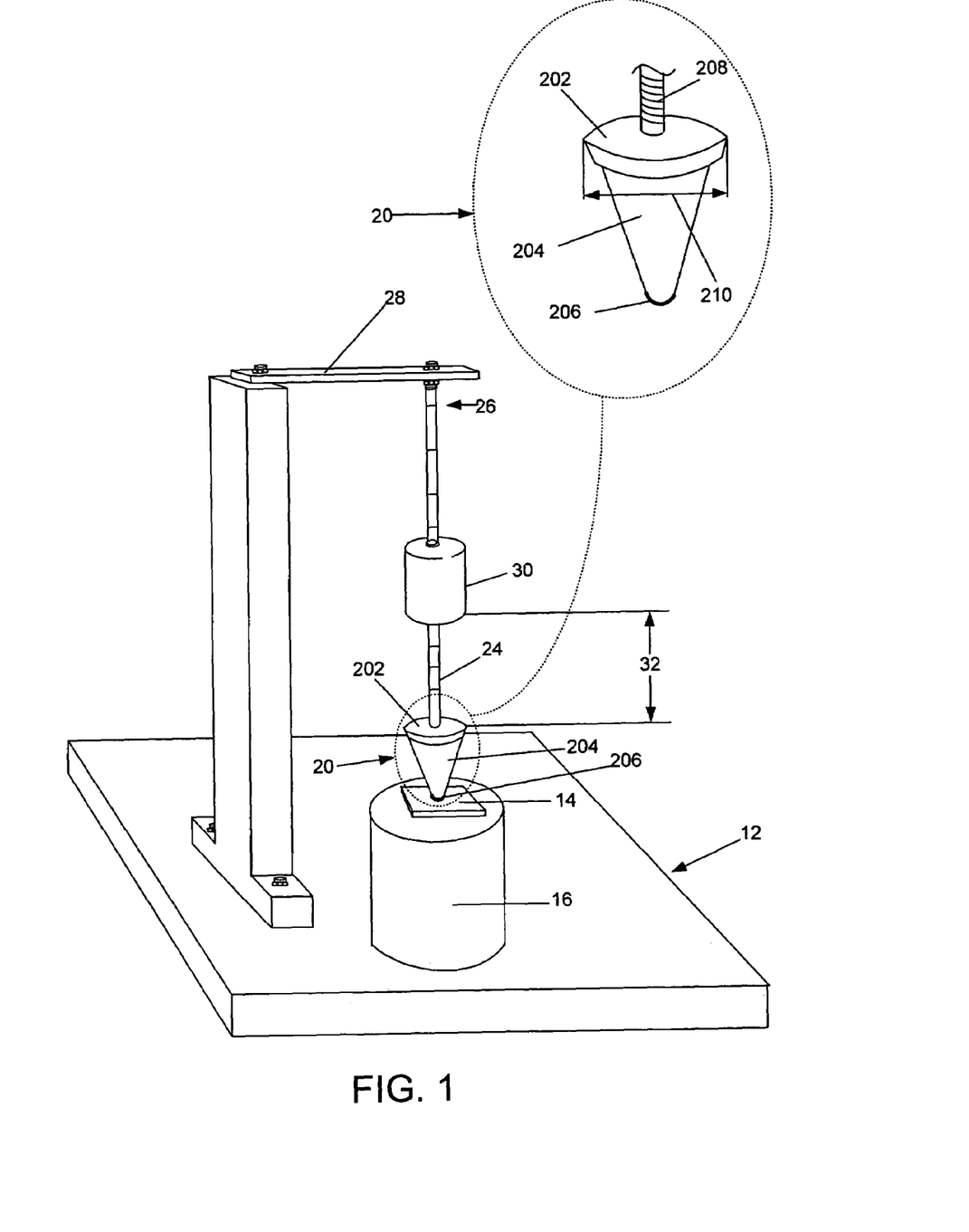
FIG. 1 is a perspective view illustrating an example of an apparatus in an embodiment of the present invention.

Referring to FIG. 1, certain embodiments of the invention generate an impact force by dropping a projectile 30 from a selected height 32 measured above a stopper assembly 20. The projectile 30 can be directed toward the stopper assembly 20 and the force of impact can be transferred through the stopper assembly 20 to a target 14. Typically, the target 14 comprises a test material or object mounted or supported on base 12 which can be held by base pedestal 16. In certain embodiments the target 14 includes a semiconductor such as a wafer, a portion of a wafer or IC die. In certain embodiments, the target 14 can be a packaged semiconductor. Larger or bulkier targets or objects 14 can be tested and it will be appreciated that other methods of support during testing can be used, including vacuum adhesion, gantries, clamps and so on. The projectile 30 can be axially mounted on a vertically oriented rod 24 and raised to the selected height above stopper assembly 20. When released from the selected height, the projectile can fall freely along the rod 24 until it impacts the stopper assembly 20. Test materials and objects can include metals, ceramics, semiconductors, semiconductor wafers, insulators, ICs, IC dies and printed circuit boards, etc. and devices, objects and combinations assembled from any suitable materials.

In certain embodiments, the stopper assembly 20 comprises a stopper washer 202 and a stopper tip body 204. The stopper assembly 20 can be fastened or otherwise attached to a vertically oriented rod 24 positioned such that a tip end 206 of tip assembly 20 contacts a selected location or area of the target 14. An upper end of the vertical rod 26 can be releasably attached to a resilient supporting gantry 28 such that the vertical height of the tip end 206 may be adjusted to permit direct contact of tip end 206 with the target 14. In certain embodiments, an upper end 208 of the stopper tip body 204 is adapted to attach to the lower end of the vertical rod 24. The upper end 208 may shaped, for example, in the form of an externally threaded shank that serves as a fastener connecting the stopper assembly 20 axially to the lower end of vertical rod 24.

The shape of the stopper tip body 204 is typically selected based on test parameters that specify, for example, the force of impact, the location of impact, size and shape of one or more areas to be impacted on the test material or object. For example, the tip can be configured such that multiple points of contact can be defined on the target 14. The stopper tip end 206 can be hardened or softened relative to the stopper tip body 204 and can be adapted to provide a selected coefficient of restitution for a test or series of test. For example, a hardened stopper tip end 206 can maintain shape and impact profile during impact even if a softer stopper tip body 204 crumples to prevent bounce and maximize energy transfer or to produce other desired effects.

The stopper washer 202 is typically formed in annular or cylindrical form having an outer diameter 210. Dimensions, shape and composition of the stopper washer 202 may be selected based on the composition, form and characteristics of the projectile 30 and stopper tip body 204. The profile of the washer is typically selected to optimize energy transfer from the falling projectile 30 through the tip of the stopper assembly 204 to the target 14. Thus, it will be appreciated that a wide range of impact characteristics can be programmed for various sized targets 14 by selective configuration of the stopper assembly 20 and projectile 30.

Figure 2:
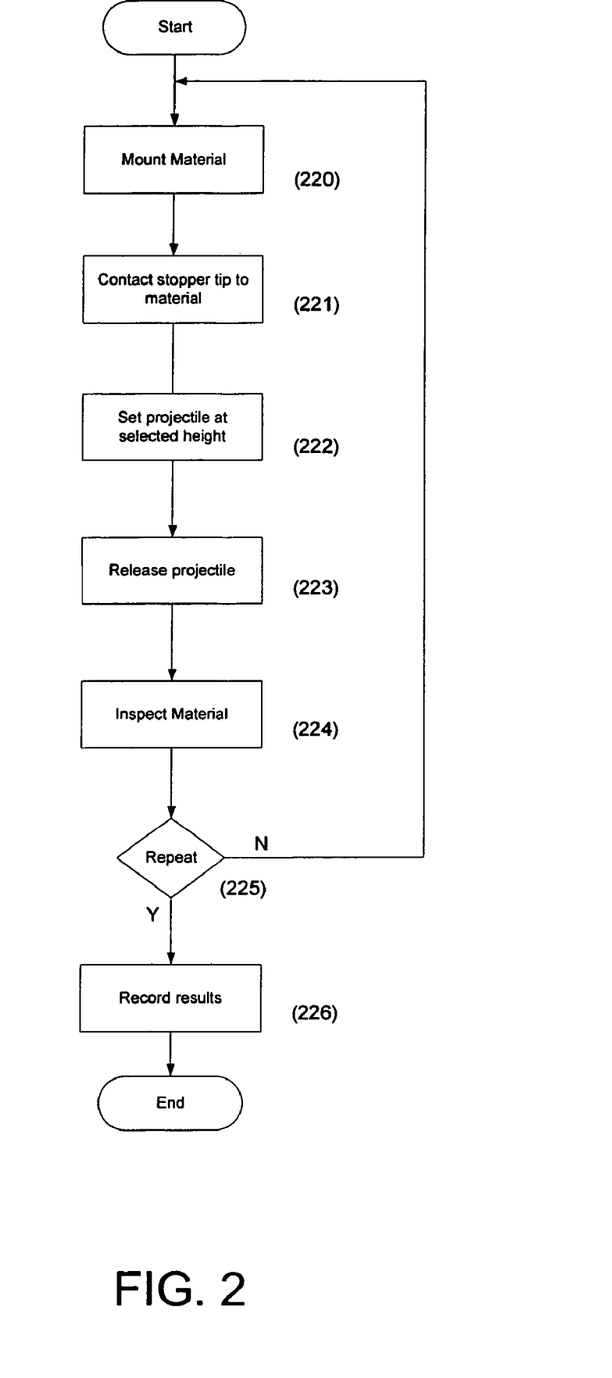
FIG. 2 is an illustrative flow chart of a method associated with the example of FIG. 1.

FIG. 2 provides a flowchart of an example of a process for dynamic impact testing using certain embodiments of the invention. At step 220, a target 14 is typically placed on base pedestal 16. At step 221, vertical rod 24 is adjusted until the end of stopper tip 206 rests on target 14; adjustment typically entails lowering vertical rod 24 from a predefined rest position. At step 222, projectile 30 is raised to a first selected height 32 and released at step 223 causing an impact between projectile 30 and stopper assembly 20. At step 224 vertical rod 24 and stopper assembly 20 can be raised to facilitate inspection of target 14 for indications of impact damage, including compression, fracture and structural failure. At step 225, a portion of steps 220-225 may be repeated as desired.

Repetition of the desired portion of steps and selection of steps for repeating is typically prescribed by test objectives. In some dynamic tests, a single sample may be repetitively subjected to impact until failure occurs. Repetition in single sample tests typically involves repositioning and realignment of the target 14 at steps 220-221. In some tests, force of impact may be increased for successive test cycles (steps 220-225). In another example, a batch of test samples can be tested at a common selected impact force. In this latter example, targets 14 are replaced after each test cycle (steps 220-225) to obtain statistical information for a desired quantity of test samples.

Where failure occurs at step 224, the height 32 from which projectile 30 was released can be recorded and can be used to calculate certain physical properties of target 14 including, for example, a force of impact at failure. In certain embodiments, where projectile 30 is released from the same selected height for each impact and the test material or object is subjected to a fixed number of impacts, the condition of the target material or object 14 is typically recorded at step 226. The step of recording 226 can be implemented automatically using, for example, optical imaging equipment 68 (see FIG. 5 and associated description below).

The energy transferred from the projectile 30 to the stopper assembly 20 during each impact can be calculated as a function of the vertical distance 32 traveled by the cylindrical projectile 30 according to the formula: $E=mgh$, where E is the energy transferred, m is the mass of projectile 30, g is acceleration due to gravity, and h is the vertical distance traveled by the by projectile 30. It will be appreciated that other factors may be considered in such calculation, such as coefficient of restitution, effect of friction, and so on. Likewise, where projectile 30 approaches stopper assembly 20 from an off-vertical angle or where a propulsion means is employed, it will be appreciated that more complex calculations may be involved in determining force of impact.

Figure 3:
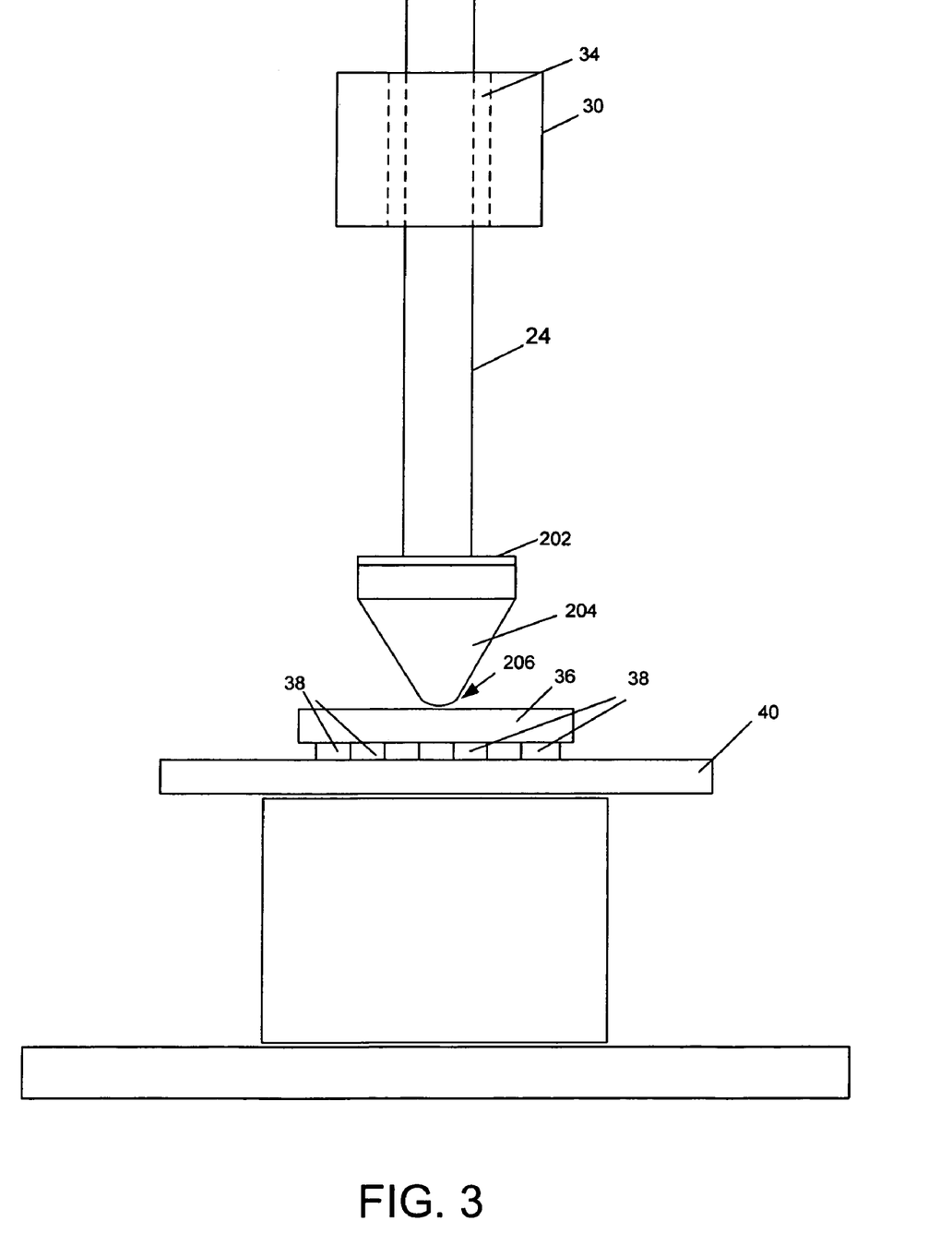
FIG. 3 shows an example of a projectile and semiconductor IC test object as used in the example of FIG. 1.

FIG. 3 shows some additional detail of the projectile in the example shown in FIG. 1. In FIG. 3, projectile 30 is cylindrical in form with an axial bore 34 such that the projectile moves freely and smoothly along the vertical cylindrical rod 24. Projectile 30 can typically be easily removed, installed or replaced on the vertical rod 24. Both the outside diameter 35 and the density of material used in constructing the projectile 30 are selectable and can be adjusted to alter the weight and density of the projectile 30 and, consequently, the force imparted to the stopper assembly 20 from any selected height 32. It will be appreciated that the shape and form can be altered as desired or stipulated in one or more test protocols. Projectiles can typically be interchanged during testing and, some embodiments, two or more projectiles can be coupled to provide greater projectile mass during testing.

Returning to FIG. 1, the tip end 206 of the stopper tip body 204 may have any desired shape and profile and can be formed as, for example, a flattened surface or pointed tip of predetermined cross-section at point of contact with the target 14. Embodiments of the invention provide apparatus adapted to receive tip ends 206 having a variety of surface shapes including, but not limited to, curved, flat, conical and irregular surfaces. The stopper tip body 204 can be manufactured from any suitable material or combination of materials including hardened steel, plastics and custom alloys. The composition and structure of the stopper tip body 204 is typically determined by the nature of testing to be performed and the nature of the target 14. FIG. 3 illustrates an embodiment in which the target test object 14 is a semiconductor IC 36 coupled by multiple solder ball contacts 38 to a printed circuit board 40.

Figure 4:
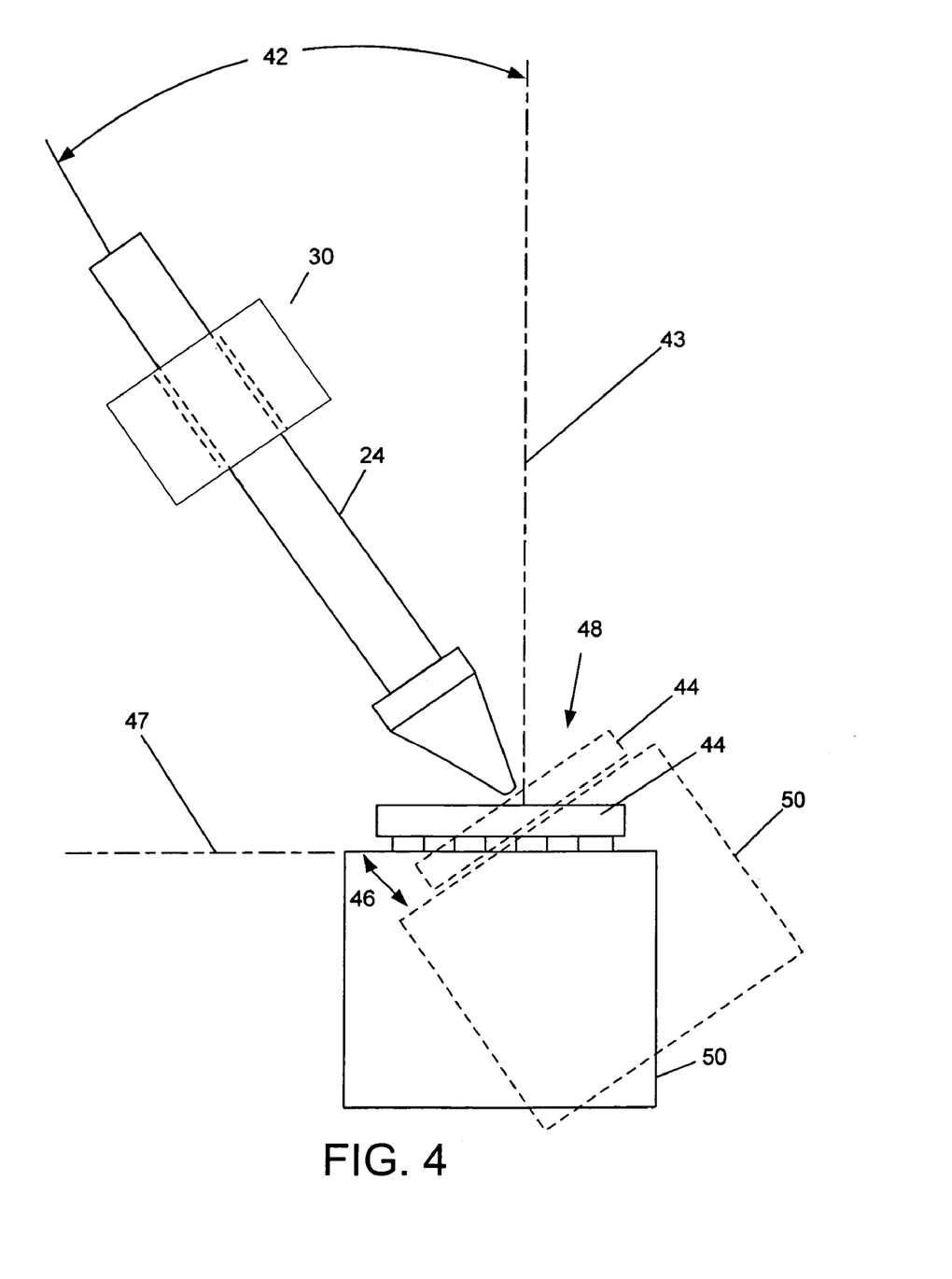
FIG. 4 shows an apparatus in which a projectile is accelerated at any selected angle in three dimensional space in one example of an embodiment of the invention.

Referring now to FIG. 4, certain embodiments provide a projectile 30 that can impact a test object or material 44 at any angle in three dimensional space. In some embodiments, vertical rod 24 may be tilted at a selected angle of between 0 and 90 degrees within a vertical plane such that impact angle is typically facilitated by a vertical rod 24 adapted to rotate through the selected angle 42 from a perpendicular 43. In certain embodiments, the base pedestal 50 may be rotated through a selected angle 46 from the horizontal 47. In certain embodiments, vertical rod 24 and base pedestal may rotate together or separately to provide any selected angle of impact in three-dimensional space.

Figure 5:
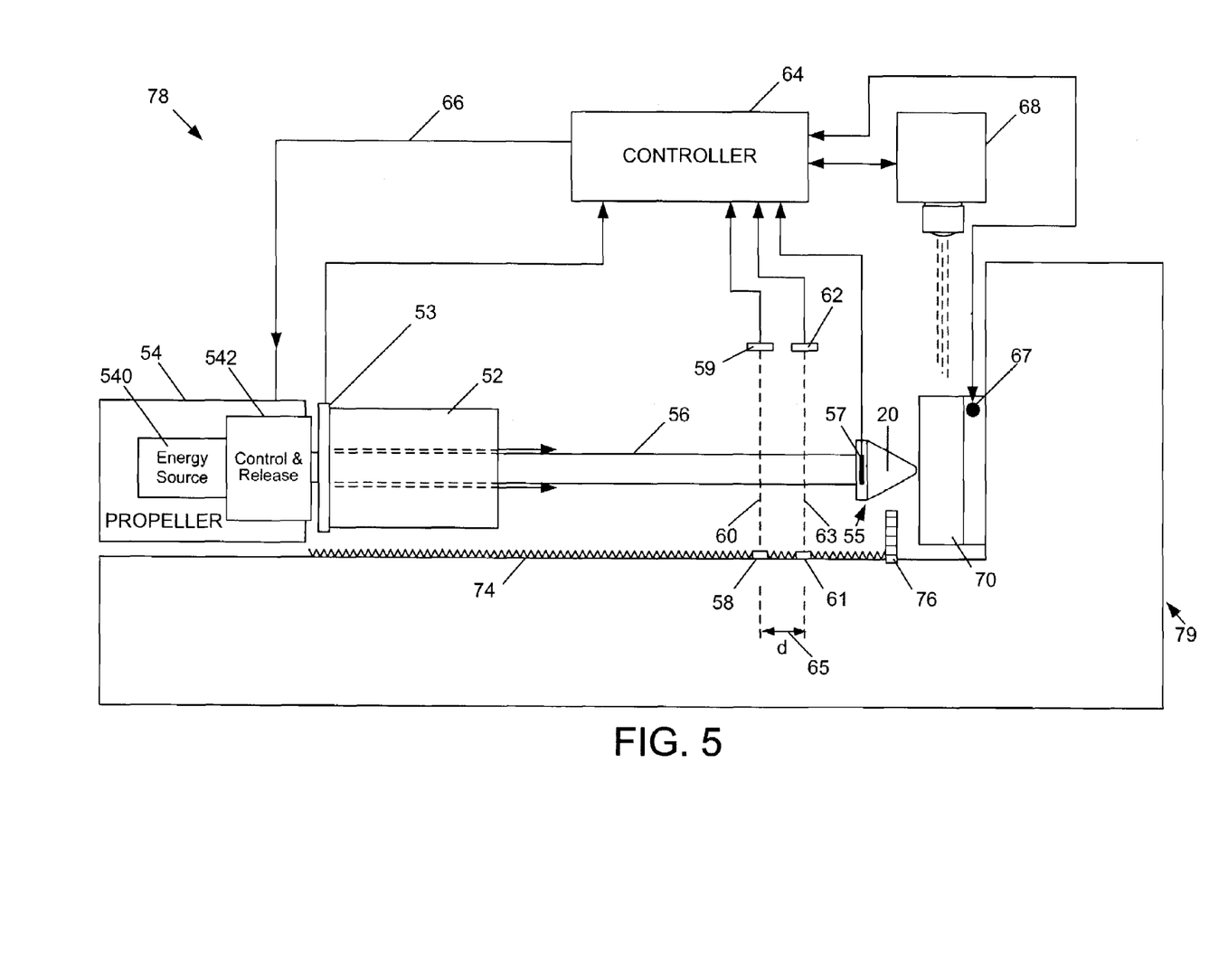
FIG. 5 illustrates an example of an embodiment that includes a fully automated test system that can use gravity or alternative energy sources for imparting energy to a projectile.

Referring now to FIG. 5, in certain embodiments an apparatus 78 comprises a projectile 52 that can be propelled by a propeller 54 along a horizontal rod 56 until it strikes a stopper assembly 20 such that stopper assembly 20 imparts a force of impact to a target 70 comprising a test material or object. Propeller 54 is typically an apparatus that controls and releases at 542 a force created by an energy source 540 such as vacuum, electric, magnetic, hydraulic, pneumatic, mechanical spring, chemical reaction or other suitable energy source. One end of the horizontal rod 56 is typically attached to the propeller 54 and the other end of the rod 56 may be adapted to receive, for example, an externally threaded shank (not shown but compare with FIG. 1) connected to the stopper assembly 20. For the purpose of this discussion, a stopper assembly identical in construction to the stopper assembly 20 shown in FIG. 1 will be considered. However, various methods of attachment as known in the mechanical arts are contemplated for use in the illustrated embodiment. The position of the assembled propeller 54, horizontal rod 56 and stopper assembly 20 can be adjusted laterally such that the stopper assembly tip end 206 is in contact with the target 70.

Embodiments of the invention permit the horizontal rod 56 and propulsion unit 54, to be operated at an incline. The energy of impact is calculated as a function of the velocity of the projectile 52 when it strikes the stopper assembly 20. A number of methods can be used to measure velocity or acceleration including, for example, Doppler systems, light emitters 58 and 61 and detectors 59 and 62, positive acceleration sensors or transducers 53 and piezoelectric force-to-voltage transducers 57. The energy of impact and other information related to the material under test can be calculated using formulae including $e=\frac{1}{2}mv^2$, where e is the energy of impact, m is the mass of the projectile 52 and v is the velocity of the projectile 52 relative to the stopper assembly 55.

By way of example, a method for measuring velocity of the projectile using light emitters and light detectors can include: (1) the projectile 52 is engaged with the propeller 54; (2) the propeller 54 accelerates the projectile; (3) the projectile 52 travels along the horizontal rod 56 until it interrupts a first focused beam of light 60 transmitted by a first light emitter 58 and a first light detector 59; (4) the first light detector 59 signals a controller 64 which initiates an internal timer; (5) the projectile 52 travels further along the horizontal rod 56 until it interrupts a second focused beam of light 63 transmitted by a second light emitter 61 and detected by a second light detector 62; (6) the second light detector signals the controller 64 which stops the internal timer; (7) the velocity is calculated by the controller by dividing the distance (d) 65 between focused light beams 60 and 63 by the elapsed time on the controller's 64 internal timer.

In some embodiments, controller 64 controls the propeller 54 by electronic connection 66 such that the projectile 52 may be launched on command of the controller 64. Imaging equipment such as a camera 68 can be connected and activated by the controller 64 to capture images of the target 70 before, during and after impact. Images may be transferred to controller 64 which is optionally programmed to measure the effect of the impact on the test object or material 70 using a pattern recognition procedure known to those skilled in the art. If the test object or material 70 has failed, the controller 64 typically records the last velocity data and calculates the corresponding energy of the impact. In certain embodiments, controller 64 may send a signal to the propeller 54 that incrementally increases the projectile 52 propulsion energy for a next impact until the material has failed. In alternative test methods, a series of impacts is performed without an increase in the propulsion energy and the controller 64 records the condition of the target 70 following each impact. In yet other test methods, a group of samples of test object or material 70 may be subjected to a common selected force. In some embodiments, controller 64 can operate sample manipulation components for automatically positioning a series of samples for impact testing. For example, samples may be maintained in a rotary or linear order such that each sample may be cycled into position for each test.

In certain embodiments, dynamic impact tests can be performed under controlled environmental conditions. In particular, heating or cooling elements and sensors 67 may be respectively controlled and monitored by controller 64 such that, for example, each of a group of samples may be tested at a desired temperature.

Optionally, a projectile retraction apparatus includes a retraction track 74, and pusher 76. The pusher 76 is driven along the track toward the propeller 54 by a retraction motor or mechanism (not shown). Pusher 76 typically contacts and pushes the projectile 52 until the projectile 52 rests against the propeller 54. Pusher 76 can then return to the furthest distance possible from the propeller 54. The pusher motor can be connected electronically 66 to the controller 64 enabling full automation of the retraction process.

Apparatus 78 is depicted in FIG. 5 as being positioned such that projectile 52 travels in a substantially horizontal direction towards the test object or material 70. However, in certain embodiments, apparatus 78 may be positioned to rest on surface 79 such that apparatus 78 functions as a vertical gravity impact tester and the projectile 52 may be accelerated using gravity force or using a combination of gravity and force generated by propeller 54. Additionally, it is contemplated that apparatus 78 may be arranged such that projectile 52 travels at any desired angle in three dimensional space towards the test object or material 70. For example, a slight angle off horizontal may be used to counteract friction and other resistive forces operating upon projectile 52.

Figure 6:
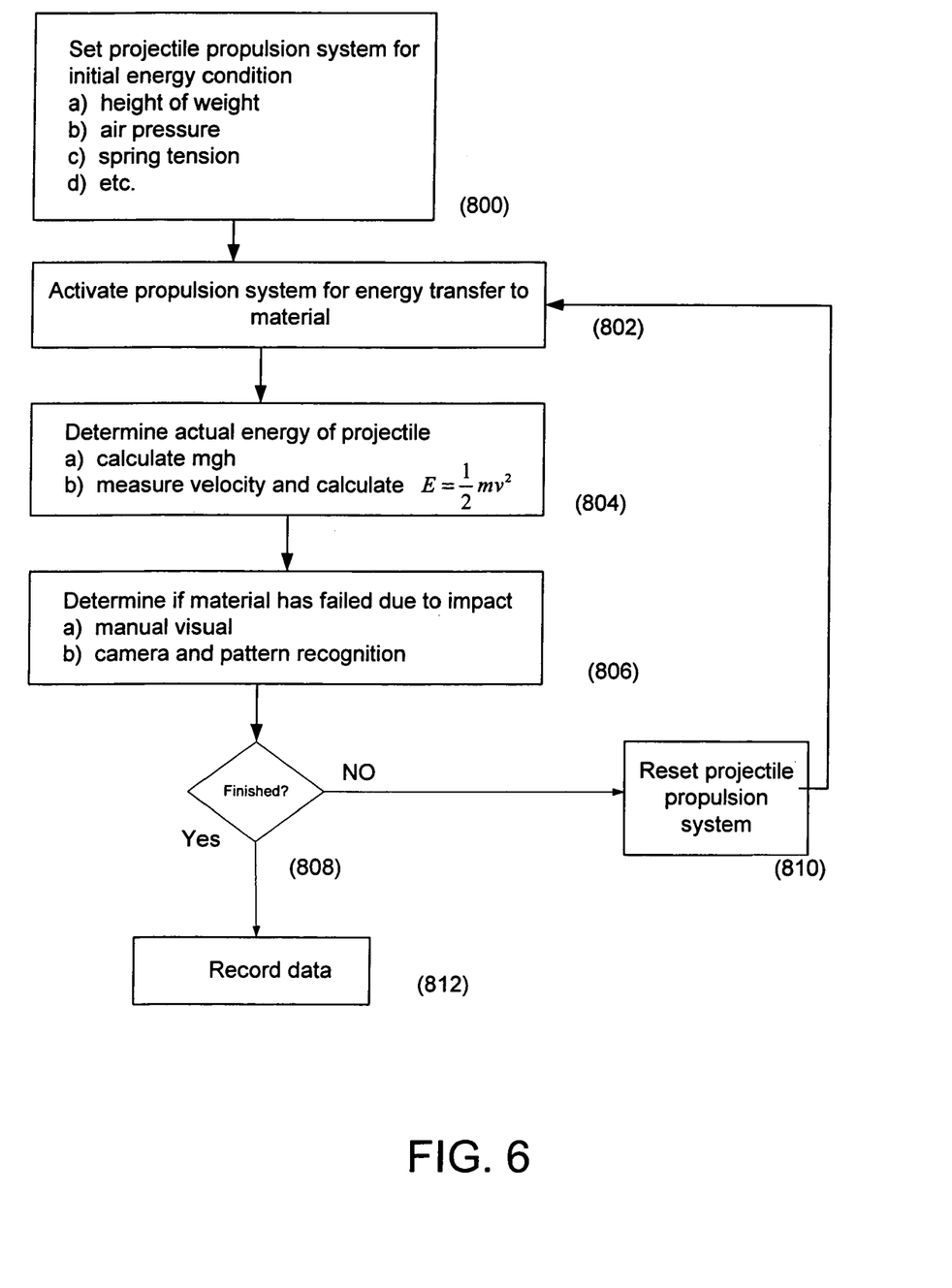
FIG. 6 is a flow chart of a method of the present invention.

FIG. 6 depicts a method for operating a dynamic impact test system, such as the system shown in the example of FIG. 5. At step 800, the force of impact imparted by the projectile 52 is typically configured. Acceleration can be used to control the force of impact by adjusting, for example, voltage, magnetic field, air/hydraulic pressure, spring tension, chemical reaction, explosion, combustion and so on. Projectile 52 mass can be used to control the force of impact by exchanging projectiles 52 or by adding or removing massive components of a configurable projectile 52.

At step 802, the propeller propels the projectile 52 and transmits the force of impact to the target 70. At step 804, energy of impact can be determined as a function of acceleration or velocity at impact. A visual inspection is typically performed at step 806 by an operator or by optical recognition systems. At step 808, it is determined whether the test should be repeated 810 or terminated 812 according to test protocol and observed results.

Figure 7:
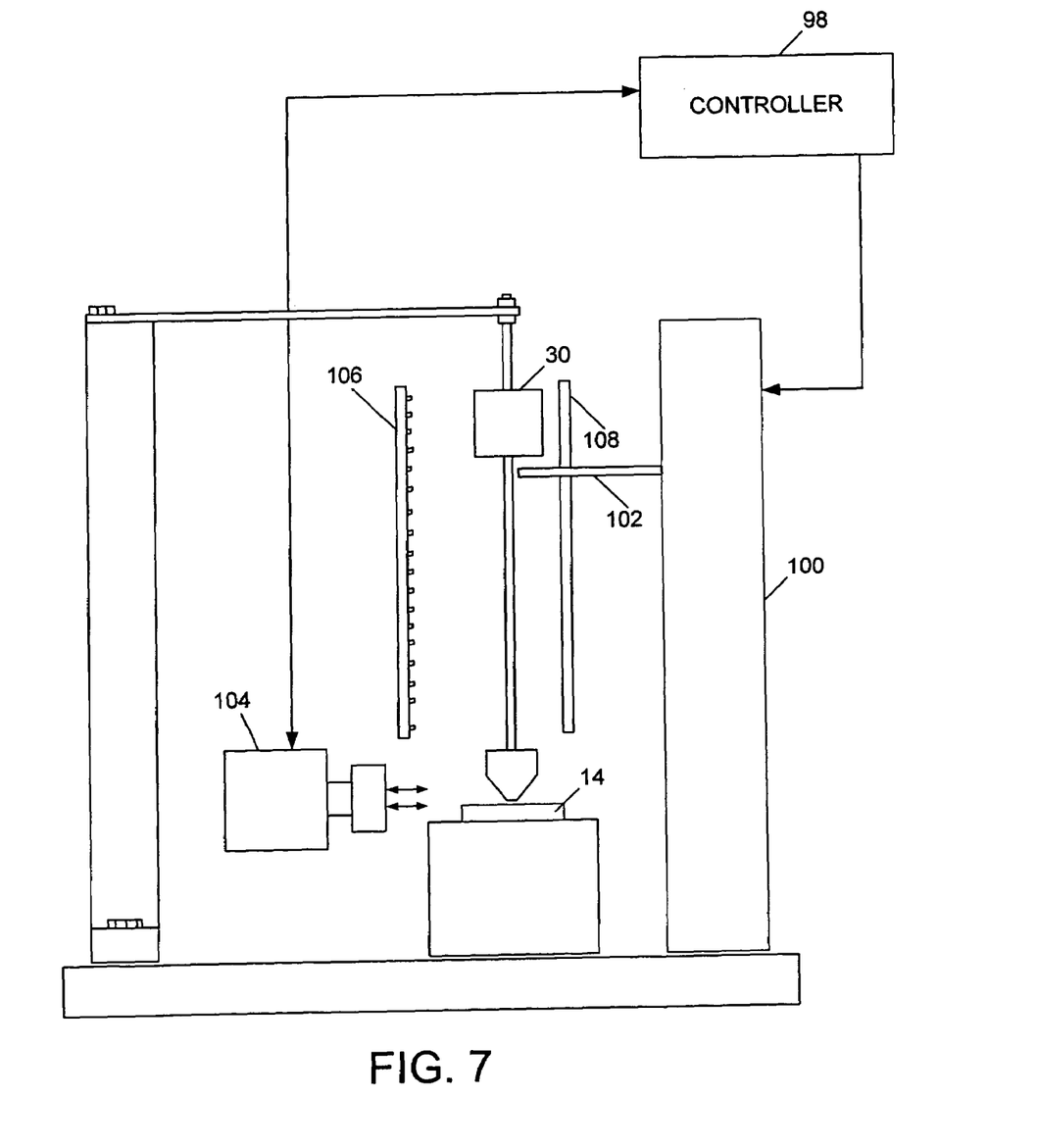
FIG. 7 shows an example of an embodiment in which an automated dynamic impact test system can use force of gravity.

Referring now to FIG. 7, in certain embodiments gravitational test apparatus such as that of FIG. 1 can optionally equipped with additional components for automating gravity-driven test system. A controller 98 may monitor and control test procedures and capture results. A projectile reset apparatus 100 may use an arm 102 to raise the projectile 30 to a desired height 32 and, on command from the controller 98, reset apparatus 100 may release the projectile 30. An optional camera 104 may be used to capture images of the test material or object and the controller 98 can use pattern recognition methods or systems known to those skilled in the art to automatically determine if the target 14 has failed. Reset apparatus 100 can include any of various types of measuring systems known to those skilled in the art for determining the height of the projectile 30 or arm 102. In one example, position information is recorded using a light beam detection apparatus, including a series of light emitters 106 and a corresponding series of light detectors 108 that permit position sensing of the projectile 30 or arm 102.

It is apparent that the above embodiments may be altered in many ways without departing from the scope of the invention. For example, one skilled in the art can appreciate that embodiments of the invention may be configured to control environmental conditions such as temperature, humidity and atmospheric pressure and composition at point of impact, for the entire test material or object or for the entire test apparatus. Further, various aspects of a particular embodiment may contain patentably subject matter without regard to other aspects of the same embodiment. Additionally, various aspects of different embodiments can be combined together. Also, those skilled in the art will understand that variations can be made in the number and arrangement of components illustrated in the above diagrams. It is intended that the appended claims include such changes and modifications.

What is claimed is:

1. An apparatus for performing dynamic impact tests, the apparatus comprising:
a projectile for delivering a desired impact force;
a stopper for transmitting the desired impact force to a predetermined location on a semiconductor target, wherein the projectile delivers the desired impact force by striking a first end of the stopper; and
a guide for directing the projectile to the stopper, the guide having a proximal end releasably attached to the first end of the stopper and a distal end, wherein
a second end of the stopper comprises a stopper tip for directing the desired impact force to the semiconductor target when the stopper tip is placed in substantial contact with the semiconductor target at the predetermined location.

2. The apparatus of claim 1, and further comprising a base for securing the semiconductor target.

3. The apparatus of claim 1, wherein the distal end is elevated relative to the proximal end, and the guide includes a release mechanism operative to release the projectile from a selected release point between the proximal end and the distal.

4. The apparatus of claim 3, wherein mass of the projectile is selectable to provide the desired impact force.

5. The apparatus of claim 3, wherein the release point is selected to provide the desired impact force.

6. The apparatus of claim 1, wherein the guide is located in a substantially horizontal plane, and wherein the projectile is accelerated to a desired velocity from the distal end in the direction of the proximal end.

7. The apparatus of claim 1, and further comprising a propeller for accelerating the projectile.

8. The apparatus of claim 7, wherein the propeller accelerates using one or more energy sources, the sources including gravitational, electric, magnetic, electromagnetic, vacuum, hydraulic, pneumatic, mechanical spring, explosive, combustive and chemically reactive sources.

9. The apparatus of claim 1, wherein the stopper tip comprises a stopper body and a tip end, the tip end being constructed from a material selected to provide a desired coefficient of restitution between the stopper tip and the semiconductor target.

10. The apparatus of claim 1, wherein the stopper tip is configured to transmit the desired impact force to a selected area defining the predetermined location, the selected area having a desired shape and a desired size.

11. An apparatus for performing dynamic impact tests, the apparatus comprising:
a projectile for delivering a desired impact force; and
a stopper for transmitting the desired impact force to a predetermined location on a semiconductor target, wherein the semiconductor target comprises a semiconductor wafer and the projectile delivers the desired impact force by striking a first end of the stopper and
wherein a second end of the stopper comprises a stopper tip for directing the desired impact force to the semiconductor target when the stopper tip is placed in substantial contact with the semiconductor target at the predetermined location.

12. An apparatus for performing dynamic impact tests, the apparatus comprising:
a projectile for delivering a desired impact force; and
a stopper for transmitting the desired impact force to a predetermined location on a semiconductor target, wherein the semiconductor target comprises one or more integrated circuit die and the projectile delivers the desired impact force by striking a first end of the stopper, and
wherein a second end of the stopper comprises a stopper tip for directing the desired impact force to the semiconductor target when the stopper tip is placed in substantial contact with the semiconductor target at the predetermined location.

13. An apparatus for performing dynamic impact tests, the apparatus comprising:
a projectile for delivering a desired impact force; and
a stopper for transmitting the desired impact force to a predetermined location on a semiconductor target, wherein the semiconductor target comprises an integrated circuit and the projectile delivers the desired impact force by striking a first end of the stopper, and wherein a second end of the stopper comprises a stopper tip for directing the desired impact force to the semiconductor target when the stopper tip is placed in substantial contact with the semiconductor target at the predetermined location.

14. A method for performing dynamic impact testing, comprising the steps of:

establishing contact between a stopper and a predetermined location on a semiconductor material;

accelerating a projectile to obtain a desired velocity, wherein the projectile has an adjustable mass;

striking the stopper with the projectile to obtain an impact force, wherein the stopper transmits the impact force to the predetermined location;

repeating the steps of establishing, accelerating, and striking a selected number of times; and adjusting the mass of the projectile prior to each repetition.

15. The method of claim 14, and further comprising adjusting the desired velocity prior to each repeating.

16. The method of claim 14, and further comprising replacing the semiconductor material prior to each repeating.

17. A method for performing dynamic impact testing, comprising the steps of:

establishing contact between a stopper and a predetermined location on a semiconductor material;

accelerating a projectile to obtain a desired velocity;

striking the stopper with the projectile to obtain an impact force, wherein the stopper transmits the impact force to the predetermined location; and inspecting the semiconductor material for impact damage, wherein inspecting includes capturing an image of the semiconductor material after each impact, and processing the image to identify impact damage.

18. A dynamic impact testing method, comprising:

establishing a contact between the tip of a stopper and a predetermined location on a surface of a test object;

when the contact is established, causing a projectile to strike the stopper at a velocity calculated to deliver a desired impact force to the test object at the predetermined location; and selectively repeating the steps of establishing and causing the projectile to strike, wherein selectively repeating includes performing a predetermined number of repetitions of the steps of establishing and causing the projectile to strike, and changing at least one of the velocity of the projectile and the mass of the projectile before each repetition, and wherein the stopper is configured to receive the desired impact force from the projectile and deliver the desired impact force to the predetermined location.

19. The dynamic impact testing method of claim 18, wherein selectively repeating includes repeating the steps of establishing and causing the projectile to strike until the test object suffers structural failure.

* * * * *